US00PP17737P2

(12) United States Plant Patent

Yomo et al.

(10) Patent No.: US PP17,737 P2

(45) Date of Patent: May 15, 2007

(54) *VERBENA* PLANT NAMED 'SUNMARIBURARE'

(50) Latin Name: *Verbena×hybrida*
Varietal Denomination: Sunmariburare

(75) Inventors: Yasunori Yomo, Kanagawa (JP); Naoto Takamura, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/264,767

(22) Filed: Nov. 1, 2005

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Verbena* plant named 'Sunmariburare', characterized by its trailing and decumbent plant habit; vigorous and freely branching growth habit; attractive light red-colored flowers; freely and continuous flowering habit; long-lasting flowers; and good garden performance.

1 Drawing Sheet

Botanical designation: *Verbena×hybrida.*
Cultivar denomination: 'Sunmariburare'.

BACKGROUND OF THE INVENTION

The present Invention relates to a new and distinct cultivar of *Verbena* plant, botanically known as *Verbena× hybrida,* and hereinafter referred to by the cultivar name Sunmariburare.

The new *Verbena* is a product of a planned breeding program conducted by the Inventors in Hokuto, Yamanashi, Japan. The objective of the breeding program is to create new trailing *Verbenas* with large and attractive flowers.

The new *Verbena* originated from a self-pollination made by the Inventors in May, 1996 of a proprietary selection of *Verbena×hybrida* identified as code number H17-8, not patented. The new *Verbena* was selected as a single plant from the resulting progeny of the self-pollination by the Inventors in a controlled environment in Hokuto, Yamanashi, Japan.

Asexual reproduction of the new cultivar by terminal cuttings at Yokaichi, Shiga, Japan since October, 1998, has shown that the unique features of this new *Verbena* are stable and reproduced true to type in successive generations.

SUMMARY OF THE INVENTION

Plants of the cultivar Sunmariburare have not been observed under all possible environmental conditions. The phenotype may vary somewhat with variations in environment such as temperature and light level without, however, any variance in genotype.

The following traits have been repeatedly observed and are determined to be the unique characteristics of 'Sunmariburare'. These characteristics in combination distinguish 'Sunmariburare' as a new and distinct cultivar of *Verbena:*

1. Trailing and decumbent plant habit.
2. Vigorous and freely branching growth habit.

3. Attractive light red-colored flowers.
4. Freely and continuous flowering habit.
5. Long-lasting flowers.
6. Good garden performance.

Compared to plants of the new *Verbena,* plants of the parent selection are more upright and not as trailing. In addition, plants of the new *Verbena* and the parent selection differ in flower color as plants of the parent selection have pink-colored flowers.

Plants of the new *Verbena* can be compared to plants of the cultivar Sunmariripi, disclosed in U.S. Plant Pat. No. 11,037. In side-by-side comparisons conducted in Yokaichi, Shiga, Japan, plants of the new *Verbena* differed from plants of the cultivar Sunmariripi in the following characteristics:

1. Plants of the new *Verbena* were larger and had longer internodes than plants of the cultivar Sunmariripi.
2. Plants of the new *Verbena* and the cultivar Sunmariripi differed in leaf shape.
3. Plants of the new *Verbena* and the cultivar Sunmariripi differed in flower coloration as plants of the cultivar Sunmariripi had pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Verbena.*

The photograph at the top of the sheet is a side perspective view of a typical plant of 'Sunmariburare'.

The photograph at the bottom of the sheet is a close-up view of typical inflorescences of 'Sunmariburare'.

DETAILED BOTANICAL DESCRIPTION

The aforementioned photographs, following observations and measurements describe plants grown during the summer in Higashiomi, Shiga, Japan in an outdoor nursery and under commercial production practices. Plants were grown in 15-cm containers and were about four months old when the photographs and description were taken. During the production of the plants, day temperatures averaged 25° C. and night temperatures averaged 15° C. Plants were pinched one time in the spring. In the following description, color references are made to The Royal Horticultural Society Colour Chart, 2001 Edition, except where general terms of ordinary dictionary significance are used.

Botanical classification: *Verbena×hybrida* cultivar Sunmariburare.

Parentage: Self-pollination of a proprietary selection of *Verbena*×hybrid identified as code number H17-8, not patented.

Propagation:

*Type.*—By terminal cuttings.

*Time to initiate roots.*—About 10 to 14 days at 20° C. to 25° C.

*Time to produce a rooted plant.*—About one month at 20° C. to 25° C.

*Root description.*—Fine, fibrous, fleshy; light brown in color.

*Rooting habit.*—Freely branching.

Plant description:

*Plant form/habit.*—Trailing and decumbent plant habit; broadly inverted triangle; vigorous growth habit. Freely branching habit with about 20 lateral branches per plant.

*Plant height.*—About 17.5 cm.

*Plant width* (*spread*).—About 84.5 cm.

*Lateral branches.*—Length: About 41.8 cm. Diameter: About 2.4 mm. Internode length: About 4.6 cm. Strength: Moderately strong. Texture: Pubescent. Color: 144A.

*Foliage description.*—Arrangement: Opposite, simple. Length: About 3.6 cm. Width: About 2 cm. Shape: Narrowly ovate. Apex: Acute. Base: Cuneate. Margin: Serrate. Texture, upper and lower surfaces: Pubescent; coarse. Venation pattern: Pinnate; reticulate. Color: Developing and fully expanded leaves, upper surface: 137B; venation, 145C. Developing and fully expanded leaves, lower surface: 137C; venation, 145C. Petiole length: About 4 mm. Petiole diameter: About 1.5 mm. Petiole texture, upper and lower surfaces: Pubescent. Petiole color, upper and lower surfaces: 145C.

Flower description:

*Flower type/habit.*—Single, star-shaped salverform flowers arranged in umbels; flowers face mostly upright. Freely flowering habit with about ten inflorescences per plant each with about ten open flowers each.

*Fragrance.*—Slightly fragrant.

*Natural flowering season.*—Continuously flowering from spring to late autumn in Japan. Flowers not persistent.

*Postproduction longevity.*—Flowers last about one week on the plant.

*Inflorescence height.*—About 3.9 cm.

*Inflorescence diameter.*—About 4.5 cm.

*Flower buds.*—Height: About 1.4 cm. Diameter: About 2.3 cm. Shape: Cylindrical. Color: 52A.

*Flowers.*—Diameter: About 1.9 cm. Depth: About 2 cm.

*Petals.*—Quantity per flower: Typically five in a single whorl; petals fused at the base into a narrow tube. Lobe length: About 7.8 mm. Lobe width: About 6.2 mm. Shape: Cordate. Apex: Emarginate. Margin: Entire. Texture, upper and lower surfaces: Smooth, glabrous; velvety. Color: Developing and fully expanded petals, upper surface: 52A. Developing and fully expanded petals, lower surface: 52C.

*Sepals.*—Quantity per flower: Typically five in a single whorl, fused; narrow tubular calyx. Length: About 1.2 cm. Width: About 0.5 mm. Shape: Lanceolate. Apex: Acute. Texture, upper and lower surfaces: Smooth, glabrous. Color, upper and lower surfaces: 145B.

*Peduncles.*—Length: About 2.7 cm. Diameter: About 1.5 mm. Texture: Pubescent. Color: 144A.

*Reproductive organs.*—Stamens: Quantity per flower: Typically four. Anther shape: Ellipsoidal. Anther length: About 0.9 mm. Anther color: 145C. Pollen amount: Scarce. Pollen color: 145C. Pistils: Quantity per flower: Typically one. Pistil length: About 1.5 cm. Stigma shape: Bi-parted. Stigma color: 144A. Style length: About 1.4 cm. Style color: 144D. Ovary color: 144C.

*Seed/fruit.*—Seed and fruit development have not been observed.

Disease/pest resistance: Plants of the new *Verbena* have not been noted to be resistant to specific pathogens and pests common to *Verbena*.

Garden performance: Plants of the new *Verbena* have been observed to have good garden performance and tolerate rain, wind and tolerated temperatures from about −3° C. to 35° C.

It is claimed:

1. A new and distinct cultivar of *Verbena* plant named 'Sunmariburare', as illustrated and described.

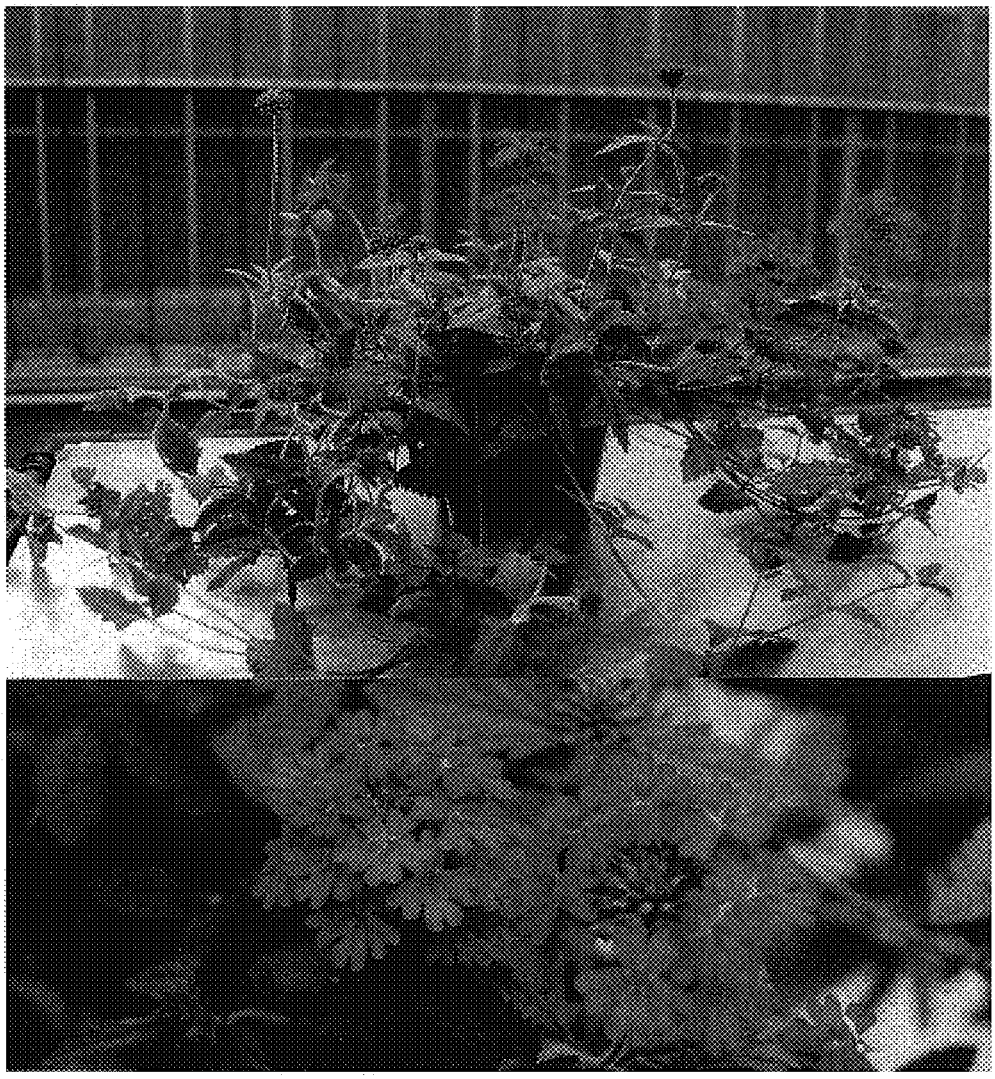

* * * * *